(12) United States Patent
Deshmukh et al.

(10) Patent No.: US 9,788,943 B2
(45) Date of Patent: Oct. 17, 2017

(54) DELIVERY SYSTEM WITH INLINE SHEATH

(71) Applicant: Medtronic, Inc., Minneapolis, MN (US)

(72) Inventors: Susheel R Deshmukh, Santa Rosa, CA (US); Joshua J. Dwork, Santa Rosa, CA (US); Patrick Griffin, Ballybrit (IE); Patrick E. Macaulay, Windsor, CA (US); A K M Masud, Mounds View, MN (US); Adam J. Shipley, San Rafael, CA (US); John P. Shanahan, Santa Rosa, CA (US); Hubert K. Young, Santa Rosa, CA (US); Stephen J. Peter, Santa Rosa, CA (US); Gustaf L P Belt, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 1003 days.

(21) Appl. No.: 13/914,802

(22) Filed: Jun. 11, 2013

(65) Prior Publication Data
US 2014/0364939 A1    Dec. 11, 2014

(51) Int. Cl.
*A61F 2/24*    (2006.01)
*A61M 25/06*    (2006.01)
*A61F 2/48*    (2006.01)

(52) U.S. Cl.
CPC .......... *A61F 2/2436* (2013.01); *A61F 2/2433* (2013.01); *A61M 25/0662* (2013.01); *A61F 2002/48* (2013.01)

(58) Field of Classification Search
CPC .. A61F 2/2436; A61F 2/2433; A61F 2002/48; A61M 25/0662
See application file for complete search history.

(56) References Cited

U.S. PATENT DOCUMENTS

| | | | |
|---|---|---|---|
| 5,824,041 A | 10/1998 | Lenker et al. | |
| 6,312,443 B1 | 11/2001 | Stone | |
| 6,629,534 B1 * | 10/2003 | St. Goar | A61B 17/0469 128/898 |

(Continued)

FOREIGN PATENT DOCUMENTS

| | | |
|---|---|---|
| CN | 1882293 | 12/2006 |
| CN | 1961847 | 5/2007 |

(Continued)

OTHER PUBLICATIONS

PCT/US2014/040431, International Search Report and Written Opinion, mailed Oct. 1, 2014.
1st Chinese Office Action, CN Appln No. 201480032359.5, dated Sep. 26, 2016.
Patent Examination Report No. 1, AU Appl. No. 2014278601, dated Jun. 21, 2016.

*Primary Examiner* — Sarah W Aleman
*Assistant Examiner* — Rachel S Highland

(57) ABSTRACT

Systems and methods for delivering and implanting heart valves are disclosed. The delivery systems can include an integrated introducer. The integrated introducer can include a sheath having an inner diameter that is smaller than the outer diameter of a delivery capsule of the delivery system and an outer diameter that is approximately equal to the outer diameter of the delivery capsule. The integrated introducer can include a hub having a hemostatic seal. The hub can have a locking mechanism configured to fix the integrated introducer in place on the delivery system.

22 Claims, 2 Drawing Sheets

(56) References Cited

U.S. PATENT DOCUMENTS

| | | |
|---|---|---|
| 7,803,131 B2 | 9/2010 | Laird et al. |
| 7,914,569 B2 | 3/2011 | Nguyen et al. |
| 8,016,877 B2 | 9/2011 | Seguin et al. |
| 2004/0267203 A1* | 12/2004 | Potter ............... A61M 25/0108 604/164.05 |
| 2005/0049667 A1 | 3/2005 | Arbefeuille et al. |
| 2006/0206192 A1 | 9/2006 | Tower et al. |
| 2007/0073391 A1* | 3/2007 | Bourang ............... A61F 2/2451 623/2.11 |
| 2011/0092910 A1 | 4/2011 | Schultz |
| 2011/0106059 A1* | 5/2011 | Graffam ............ A61M 25/0097 604/544 |
| 2011/0208296 A1 | 8/2011 | Duffy et al. |
| 2011/0245917 A1 | 10/2011 | Savage et al. |
| 2011/0251682 A1 | 10/2011 | Murray, III et al. |
| 2011/0251683 A1 | 10/2011 | Tabor |
| 2011/0257733 A1 | 10/2011 | Dwork |
| 2011/0264198 A1 | 10/2011 | Murray, III et al. |
| 2012/0022629 A1* | 1/2012 | Perera .................... A61F 2/2418 623/1.11 |
| 2012/0035717 A1* | 2/2012 | Duffy .................... A61F 2/2427 623/2.11 |

FOREIGN PATENT DOCUMENTS

| | | |
|---|---|---|
| CN | 201578402 | 9/2010 |
| CN | 102038998 | 5/2011 |
| CN | 102843994 | 12/2012 |
| EP | 2322122 | 5/2011 |
| WO | WO2008/031103 | 3/2008 |
| WO | WO2011/102968 | 8/2011 |

* cited by examiner

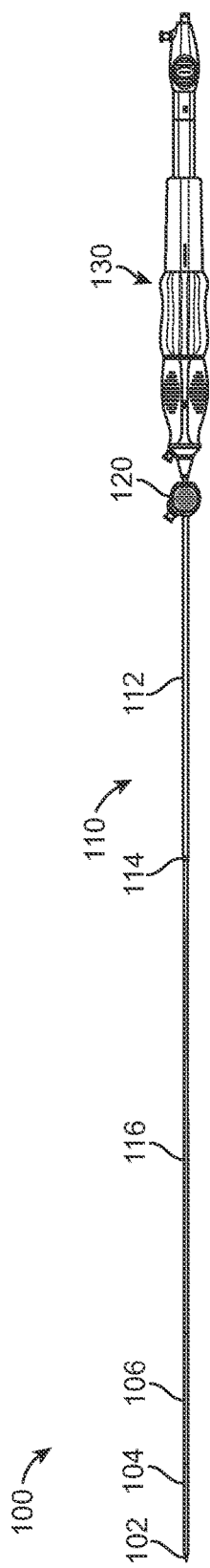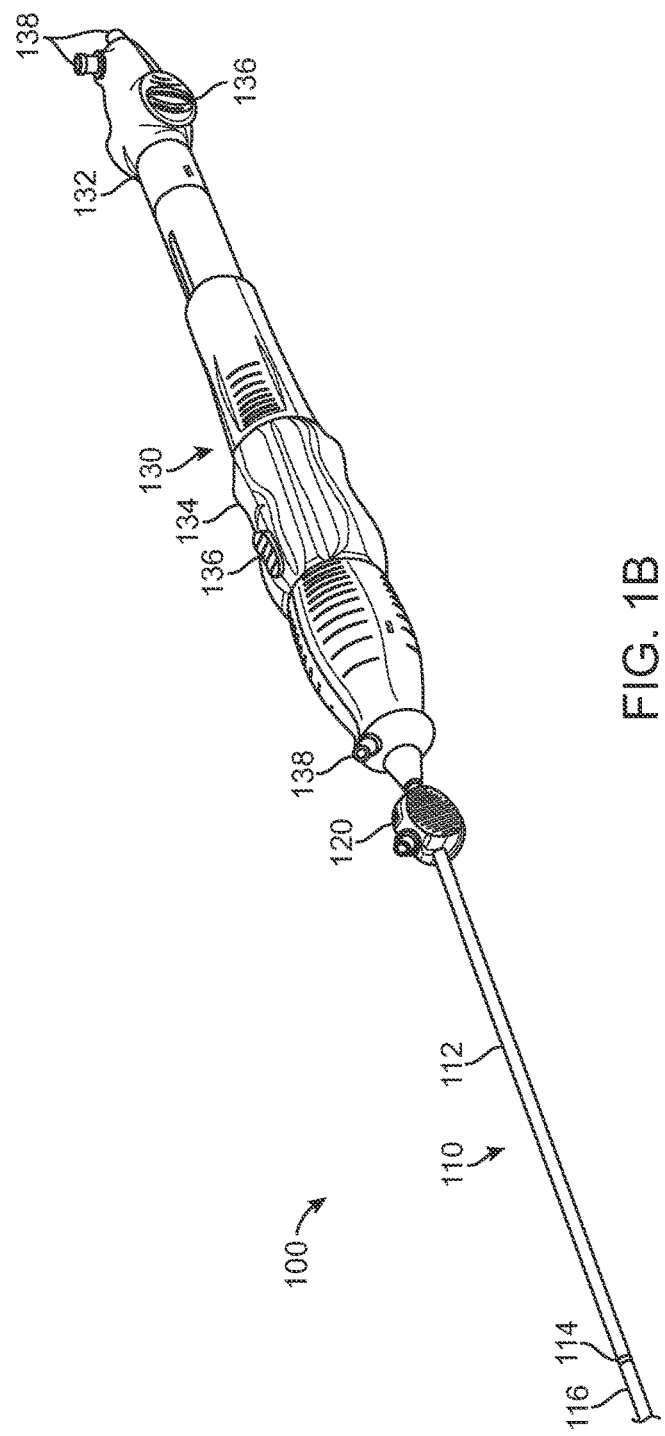

US 9,788,943 B2

DELIVERY SYSTEM WITH INLINE SHEATH

BACKGROUND

Field

The present disclosure relates to heart valve delivery systems and methods of delivering and implanting heart valves. More specifically, the present disclosure relates to delivery systems with an integrated introducer. The integrated introducer can include a hub having a hemostatic seal.

Background

Minimally invasive approaches have been developed to facilitate catheter-based implantation of valve prostheses on the beating heart, intending to obviate the need for the use of classical sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a lumen within the body, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

With regard to the structure of the heart valve prosthesis itself, U.S. Pat. No. 7,914,569 to Nguyen et al. describes an example prosthesis for percutaneous transluminal delivery. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

Other techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter can be transcatheterally advanced toward the native valve, where it can be either forcefully deployed using a balloon catheter, or, alternatively, passively deployed using a self-expandable system.

Typical introducer systems contain an access lumen for introduction of transcatheter medical devices, a hub for connection to syringes and other peripheral devices, and a hemostatic valve to prevent blood loss from the lumen of the introducer sheath. The profile, or outer diameter, of the introducer can be a limiting factor in whether certain transcatheter medical devices can be introduced into a patient because sufficient vessel size is necessary to accommodate the introducer sheath. In order to extend the availability of transcatheter devices to patients with smaller vessel sizes, an introducer with a smaller profile is desired.

BRIEF SUMMARY

The present disclosure relates to delivery systems for medical devices, for example, prosthetic heart valves. The delivery systems disclosed herein can include a handle, a delivery capsule, an inner lumen connecting the handle and the delivery capsule, and an integrated introducer. In certain embodiments, the integrated introducer can be slidably disposed about, and move freely along, the inner lumen. Generally, the inner diameter of the integrated introducer is smaller than the maximum outer diameter of the delivery system, and the outer diameter of the integrated introducer is approximately equal to the maximum outer diameter of the delivery system.

In certain embodiments, the integrated introducer can include a sheath where the inner diameter of the sheath is smaller than the outer diameter of a delivery capsule of the delivery system and the outer diameter of the sheath is approximately equal to the outer diameter of the delivery capsule. This relationship can provide a smooth transition between the delivery capsule and the sheath of the integrated introducer. In certain embodiments, the outer diameter of the sheath can be larger or smaller than the outer diameter of the delivery capsule. The integrated introducer can reduce the overall profile of the combined delivery system and introducer in comparison to traditional, separate introducer and delivery systems. This can eliminate the need for a separate introducer component to be used with the delivery system. Minimizing the access profile of the delivery system can increase the potential patient population and reduce trauma associated with transluminal delivery of medical devices.

In certain embodiments, the integrated introducer can include a hub having a hemostatic valve located within an interior space of the hub. The hemostatic valve can fit against a retention element to provide a tight seal. The hemostatic seal can maximize leak pressure while reducing tracking force. In certain embodiments, the hub can include a locking element configured to lock the integrated introducer at a location along the inner lumen of the delivery system.

Integrated introducers are also disclosed. In certain embodiments, the integrated introducer can include a sheath and a hub having a hemostatic valve located within an interior space of the hub. In certain embodiments, the sheath can include a rigid ring located at a distal end of the sheath. The rigid ring can prevent the integrated introducer from riding up over the delivery capsule of the delivery system. In certain embodiments, the inner diameter of the sheath can be smaller than an outer diameter of the delivery capsule and the outer diameter of the sheath can be approximately equal to an outer diameter of the delivery capsule. In certain embodiments, the outer diameter of the sheath can be larger or smaller than the outer diameter of the delivery capsule.

Methods of delivering a medical device are also disclosed. A delivery system having an integrated introducer such as those described herein can be inserted into a body lumen, where the delivery capsule contacts the sheath (or rigid ring tip) of the integrated introducer in an insertion configuration. The delivery capsule can be advanced distally such that it breaks contact with the integrated introducer. The delivery capsule can be maneuvered through the vasculature to a deployment location, and the medical device can be deployed at the deployment location. The delivery system can then be removed from the body lumen.

In certain embodiments, the method of delivering the medical device can include disconnecting the integrated introducer from the handle of the delivery system. In certain embodiments, a hub connected to the sheath can include a locking element, and the method can include sliding the integrated introducer along the inner lumen or stability member of the delivery system and locking the integrated introducer in place by activating the locking element to grip the inner lumen or stability member.

BRIEF DESCRIPTION OF THE DRAWINGS

The accompanying figures, which are incorporate herein, form part of the specification and illustrate embodiments of prosthetic valves having directionally distinguishable markers. Together with the description, the figures further to serve to explain the principals of and allow for the making and using of the prosthetic valves described herein. These figures are intended to be illustrative, not limiting. Although the disclosure is generally described in the context of these embodiments, it should be understood that it is not intended to limit the scope of the disclosure to these particular embodiments. In the drawings, like reference number indicate identical or functionally similar elements.

FIG. 1A illustrates a delivery system including an integrated introducer, according to an embodiment.

FIG. 1B illustrates a handle and inline sheath introducer of a delivery system, according to an embodiment.

DETAILED DESCRIPTION

Figure 2:
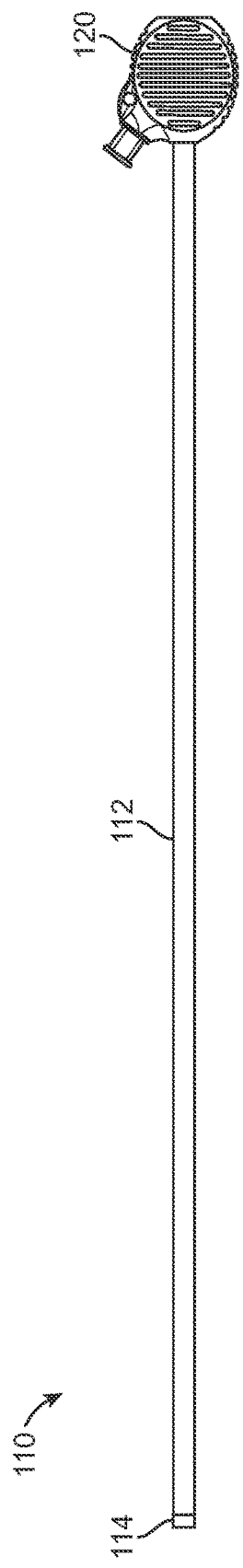
FIG. 2 illustrates an inline sheath introducer, according to an embodiment.

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting.

Further, it is understood that the devices and methods described below can be implemented in many different embodiments of hardware. Any actual hardware described is not meant to be limiting. The operation and behavior of the device, systems, and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

FIG. 1A illustrates delivery system 100, according to an embodiment. Delivery system 100 can include distal tip 102, delivery capsule 104, and inner lumen 106. In certain embodiments, delivery system 100 can include integrated introducer 110, which can be configured about inner lumen 106. In certain embodiments, integrated introducer 110 can include inline sheath 112, tip ring 114, and hub 120. In certain embodiments, delivery system 100 can include stability member 116. In certain embodiments, delivery system 100 can include handle 130. The components of delivery system 100 can be made of any suitable materials. For example, the components can be biocompatible plastics, metals and/or composite materials.

In certain embodiments, inner lumen 106 can connect handle 130 and delivery capsule 104. By manipulating a control mechanism on handle 130, inner lumen 106 can be advanced distally and retracted proximally. This, in turn, can advance and retract delivery capsule 104 and distal tip 102. In certain embodiments, delivery capsule 104 can house a prosthetic heart valve (not shown). The prosthetic heart valve can be configured to be collapsible and expandable such that it can be compressed to fit within delivery capsule 104 during delivery and expanded, either manually or by self-expansion, upon deployment. In certain embodiments, distal tip 102 can be tapered to facilitate guiding the delivery system through the vasculature while preventing trauma.

FIG. 1B illustrates integrated introducer 110 and handle 130 of delivery system 100, according to an embodiment. In certain embodiments, integrated introducer 110 can include inline sheath 112, tip ring 114, stability member 116, and hub 120. In certain embodiments, inline sheath 112 and/or stability member 116 can be detached and reattached with the handle 130.

In certain embodiments, inline sheath 112 can be slidably disposed about stability member 116, which can extend from handle 130 to delivery capsule 104 (shown in FIG. 1A). In certain embodiments, the materials of stability member 116 and inline sheath 112 can reduce friction between the components, which can allow inline sheath 112 to slide easily along stability member 116. In certain embodiments, inline sheath 112 can include a liner or lubricant to reduce friction with stability member 116. In certain embodiments, stability member 116 can be made of a material that is more rigid than inline sheath 112. For example, in certain embodiments, stability member 116 can be a rigid plastic and inline sheath 112 can be a flexible plastic. In certain embodiments, stability member 116 can be disconnected from handle 130 and reconnected to handle 130. In certain embodiments, an outer diameter of stability member 116 can be approximately equal to an outer diameter of delivery capsule 104. In certain embodiments, an outer diameter of stability member 116 can be larger or smaller than an outer diameter of delivery capsule 104. In certain embodiments, stability member 116 and inline sheath 112 can be a single component, which can include any or all of the features of stability member 116 and inline sheath 112 described herein.

In certain embodiments, inline sheath 112 can include tip ring 114. In certain embodiments, tip ring 114 can be located at a distal end of inline sheath 112 and configured to mate with delivery capsule 104. In certain embodiments, a locking fit can be formed between tip ring 114 and delivery capsule 104, for example, by means of a "hex" fit between a distal end of tip ring 114 and a proximal end of delivery capsule 104. This can facilitate transmitting torque from inline sheath 112 to delivery capsule 104. In certain embodiments, tip ring 114 can be made of a rigid material. This can prevent inline sheath 112 from expanding and moving over delivery capsule 104 during delivery, which can cause vascular complications. Tip ring 114 is explained in further detail below with reference to FIG. 2.

In certain embodiments, handle 130 can include proximal portion 132 and distal portion 134. In certain embodiments, handle 130 can include one or more buttons 136. In certain embodiments, buttons 136 can be manipulated to advance and/or retract parts of delivery system 100, for example, inner lumen 106 (shown in FIG. 1A). It is understood that buttons 136 could be other actuation mechanisms, such as knobs, switches, thumbwheels, etc. In certain embodiments, portions of handle 130 can move relative to each other, for example, by sliding, twisting, or rotating. In certain embodiments, handle 130 can include gripping features, for example, notches or grooves on the surface of handle 130.

In certain embodiments, handle 130 can include one or more ports 138. Ports 138 can be used as flush ports, to introduce fluids into delivery system 100, or connect peripheral devices to delivery system 100, for example.

FIG. 2 illustrates integrated introducer 110, according to an embodiment. Integrated introducer 110 can include inline sheath 112, tip ring 114, and hub 120. In certain embodiments, tip ring 114 can be located at a distal end of inline sheath 112 and hub 120 can be located at or near a proximal end of inline sheath 112.

Inline sheath 112 can be made of any suitable material, for example, but not limited to, biocompatible plastic. In certain embodiments, inline sheath 112 can include flexible and rigid portions. For example, a proximal portion of inline sheath 112 can be rigid and a distal portion of inline sheath can be flexible. In certain embodiments, inline sheath 112 can be made of a coil reinforced shaft, for example, having a biocompatible polymer jacket. In certain embodiments, the coil reinforcing element can be a different polymer than the jacket, or a metallic element. In certain embodiments, inline sheath 112 can be made of a braided shaft. In certain embodiments, inline sheath 112 can include a welded coil end to prevent flaring. In certain embodiments, inline sheath 112 can be configured as described in U.S. Publication No. 2011/0208296, which is incorporated by reference herein in its entirety. In certain embodiments, inline sheath 112 can be coated with a low friction polymer (e.g., parylene) or a lubricant (e.g., silicone fluid) to minimize the force needed to slide along inner lumen 106 and/or stability member 116.

In certain embodiments, inline sheath 112 can be an expandable sheath. For example, inline sheath 112 can incorporate features described in U.S. patent application Ser. No. 13/791,110, which is incorporated by reference herein in its entirety. In certain embodiments, inline sheath 112 can have a composite design, capable of expanding upon engagement with the capsule of the delivery system. For example, inline sheath 112 can be a slotted tube made of nitinol, which can expand to fit over the capsule. In certain embodiments, expandable inline sheath 112 can include a hemostatic seal using a funnel and valve design. The ability of inline sheath 112 to expand can allow the user to leave integrated introducer 110 in the body as a standalone introducer after detaching it from the handle, or allow the user to remove integrated introducer 110 and use a standard introducer.

In certain embodiments, inline sheath 112 can be steerable. For example, the delivery system can include wires (not shown) that run generally parallel to the longitudinal axis of integrated introducer 110. In certain embodiments, the wires can be pre-shaped, and in certain embodiments, the wires can be operated by a control mechanism. The wires can be controlled, for example, by a mechanism in the handle or in hub 120. Manipulating the wires can cause inline sheath 112 to bend, allowing it to be steered through the vasculature.

In certain embodiments, inline sheath 112 can include tip ring 114. Tip ring 114 can prevent flaring of inline sheath 112 so that inline sheath 112 cannot slide over the delivery capsule of the delivery system. In certain embodiments, tip ring 114 can mate with the delivery capsule, for example, by friction fit or via an element on each component, for example complementary snap-fit components. In certain embodiments, tip ring 114 can be made of a rigid material, for example, a plastic or metal band. In certain embodiments, tip ring 114 can be made of solid metal and welded to inline sheath 112. In certain embodiments, tip ring 114 can be a high durometer polymer or composite material. In certain embodiments, tip ring 114 can be made of multiple materials, for example, a soft polymer and a rigid metal. In certain embodiments, tip ring 114 can be a radiopaque material. This can facilitate locating tip ring 114 using medical imaging during delivery of a medical device.

Figure 3A:
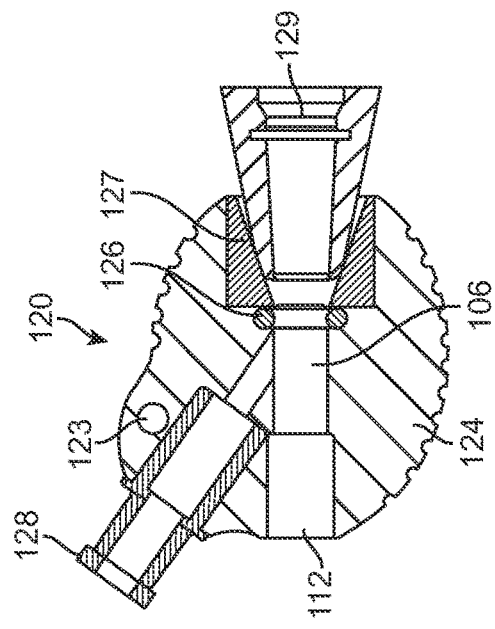
FIG. 3A illustrates a hub, according to an embodiment.

FIG. 3A illustrates hub 120, according to an embodiment. Hub 120 can be made of any suitable material, for example, rubber or plastic. In certain embodiments, hub 120 can be made from a molded material. In certain embodiments, exterior surface 122 of hub 120 can have ridges 121, which can facilitate gripping hub 120. In certain embodiments, other gripping mechanisms, for example, a textured exterior surface 122 can be included on hub 120.

In certain embodiments, hub 120 can include one or more suture hole 123. In certain embodiments, one or more sutures can be threaded through and/or tied about suture hole 123. The sutures can also be affixed to the patient, which can attach hub 120 to the patient and maintain the position of hub 120 relative to the patient.

In certain embodiments, hub 120 can include cavity 125. In certain embodiments, cavity 125 can extend entirely through hub 120 from a distal end to a proximal end. As shown, for example in FIG. 3B, cavity 125 can provide an entry point for inner lumen 106 and inline sheath 112 into hub 120. In certain embodiments, inline sheath 112 can be attached to hub 120.

In certain embodiments, hub 120 can include valve 128. In certain embodiments, valve 128 can be connected to inner lumen 106, inline sheath 112, and/or stability member 116. In certain embodiments, valve 128 can be a one-way flush valve. In certain embodiments, valve 128 can be a stop-cock (e.g., a three-way stop-cock valve) with a tube connected to hub 120. In certain embodiments, valve 128 can facilitate attachment of peripheral devices to hub 120. In certain embodiments, fluid, dye, etc., can be introduced into the delivery system, for example into inner lumen 106, inline sheath 112, and/or stability member 116 via valve 128.

Figure 3B:
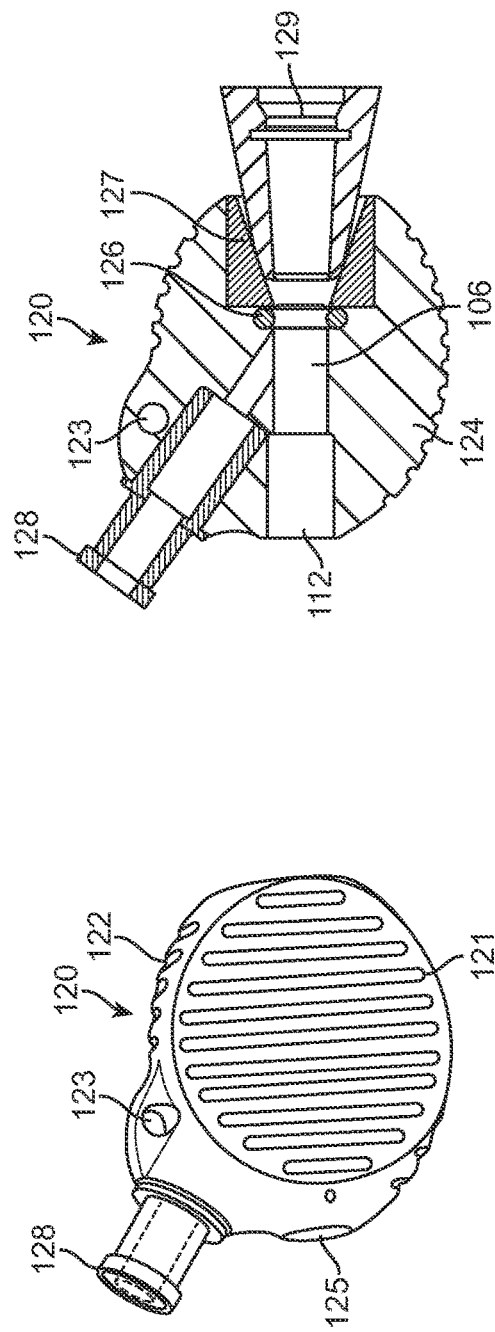
FIG. 3B illustrates an interior view of a hub, according to an embodiment.

FIG. 3B illustrates an interior view of hub 120, according to an embodiment. In certain embodiments, hub 120 can include suture hole 123 and valve 128. In certain embodiments, inline sheath 112 can extend within an interior space 124 of hub 120. In certain embodiments, inner lumen 106 can extend within interior space 124 of hub 120.

In certain embodiments, hemostatic valve 126 can be located within interior space 124 of hub 120. Hemostatic valve 126 can be made of any suitable material, for example rubber, silicone, or plastic. In certain embodiments, hemostatic valve 126 can have a coating, for example, a waterproof coating. In certain embodiments, hemostatic valve 126 can be an "o-ring" type valve. In certain embodiments, hemostatic valve 126 can be other known types of valves. In certain embodiments, retention element 127 can be in contact with hemostatic valve 126. Retention element 127 can facilitate hemostatic valve 126 in creating a seal.

In certain embodiments, connector 129 can connect hub 120 with the handle of the delivery system (not shown). In certain embodiments, inner lumen 106 can extend through connector 129 to connect with the handle.

In certain embodiments, hub 120 can be a locking hub, which can maintain its position on the delivery system. In certain embodiments, hub 120 can include a locking actuator (button, switch, wheel, etc.), which can be activated to lock hub 120 to inner lumen 106 or the stability member (not shown). In certain embodiments, the locking actuator can be coupled to exterior surface 122 of hub 120. In certain embodiments, activating the locking actuator can move a locking element within interior space 124 of hub 120, which can create a frictional interaction between the locking element and the delivery system. The frictional interaction can prevent hub 120, and thereby integrated introducer 110, from moving proximally and distally along, or rotating about, the delivery system. In certain embodiments, activating the locking actuator can engage tooth-like components to lock hub 120 in place along inner lumen 106 or stability member 116.

Methods of delivering a medical device are also disclosed. In certain embodiments, the medical device can be a heart valve prosthesis that is delivery through the vasculature. In certain embodiments, a delivery system having an integrated introducer such as those described herein can be used to deliver delivery the medical device. In certain embodiments, the integrated introducer can include a sheath having an outer diameter that is approximately equal to the outer diameter of a delivery capsule, which can reduce the overall diameter of the delivery system.

In certain embodiments, the delivery system can be inserted into a body lumen. In certain embodiments, the delivery system can have an insertion configuration where the delivery capsule contacts the sheath (or rigid ring tip) of the integrated introducer. The rigid ring tip can allow the sheath to fit against the delivery capsule but prevent the sheath from riding up over the delivery capsule of the delivery system. In certain embodiments, the ring tip can be made of a radiopaque material so that it can be located using medical imaging during the delivery procedure. In certain embodiments, the delivery system can be advanced distally such that contact between the delivery capsule and the integrated introducer is broken.

In certain embodiments, the integrated introducer can be disconnected from the handle. In certain embodiments, the integrated introducer can slide along the inner lumen of the delivery system or along a stability member. In certain embodiments, the integrated introducer can be locked in place by activating a locking element, for example, on a hub of the integrated introducer. In certain embodiments, the delivery capsule can be maneuvered through the vasculature to a deployment location, and the medical device can be deployed at the deployment location. In certain embodiments, a steering mechanism can control wires to maneuver the delivery system. The delivery system can be removed from the body lumen after deploying the medical device. In certain embodiments, delivery methods can be used such as those described in U.S. Publication No. 2011/0251683, which is incorporated by reference herein in its entirety.

The foregoing description has been presented for purposes of illustration and description. It is not intended to be exhaustive or to limit the precise embodiments disclosed. Other modifications and variations may be possible in light of the above teachings.

The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A delivery system for a medical device comprising:
   a handle;
   a delivery capsule configured to hold the medical device in a compressed delivery state comprising an outer diameter, a proximal end, and a distal end;
   an inner lumen connecting the handle and the delivery capsule; and
   an integrated introducer slidably disposed about the inner lumen, the integrated introducer comprising:
      a sheath comprising a proximal end, a distal end, an inner diameter, and an outer diameter; and
      a hub located at the proximal end of the sheath,
   wherein the inner diameter of the sheath is smaller than the outer diameter of the delivery capsule, and
   wherein the distal end of the sheath is rigid and cannot slide over any portion of the delivery capsule.

2. The delivery system of claim 1, wherein the outer diameter of the sheath is approximately equal to the outer diameter of the delivery capsule.

3. The delivery system of claim 1, wherein the distal end of the sheath further comprises a rigid ring configured to mate with the proximal end of the delivery capsule.

4. The delivery system of claim 3, wherein the ring is made of a radiopaque material.

5. The delivery system of claim 1, wherein the proximal end of the delivery capsule contacts the distal end of the sheath in an insertion configuration.

6. The delivery system of claim 5, wherein the delivery capsule is located distally from the distal end of the sheath in a delivery configuration.

7. The delivery system of claim 1, wherein the integrated introducer is configured to be disconnected from the handle.

8. The delivery system of claim 1, wherein the sheath comprises a flexible distal portion and a rigid proximal portion.

9. The delivery system of claim 1, further comprising a tubular stability member located between the inner lumen and the sheath.

10. The delivery system of claim 9, wherein the integrated introducer is slidable along and around the stability member.

11. The delivery system of claim 1, wherein a distal portion of the sheath is expandable.

12. The delivery system of claim 1, further comprising a plurality of wires running along an axis of the integrated introducer, wherein the wires are connected to a steering element located in the handle.

13. The delivery system of claim 1, wherein the hub further comprises:
   an exterior surface;
   an interior space; and
   a hemostatic valve located within the interior space.

14. The delivery system of claim 13, wherein the inner lumen extends through the interior space of the hub, and
   wherein the hub further comprises a one-way flush valve connected to the inner lumen.

15. The delivery system of claim 13, wherein the hemostatic valve fits against a retention element.

16. The delivery system of claim 13, wherein the hub further comprises a suture hole through the exterior surface of the hub.

17. The delivery system of claim 1, wherein the hub further comprises a locking element configured to lock the integrated introducer at a location along the inner lumen.

18. An integrated introducer for a medical device delivery system comprising:
   a sheath comprising a proximal end, a distal end, an inner diameter, and an outer diameter; and
   a hub located at the proximal end of the sheath comprising:
      an exterior surface;
      an interior space; and
      a hemostatic valve located within the interior space,
   wherein an inner diameter of the sheath is smaller than an outer diameter of a delivery capsule of the delivery system, and
   wherein the distal end of the sheath is rigid and cannot slide over any portion of the delivery capsule.

19. The integrated introducer of claim 18, wherein the outer diameter of the sheath is approximately equal to the outer diameter of the delivery capsule.

20. A method of delivering a medical device comprising:
   providing a delivery system for delivering the medical device, the delivery system comprising:
      a handle;
      a delivery capsule comprising an outer diameter, a proximal end, and a distal end, the delivery capsule being configured to hold the medical device in a compressed delivery state;
      an inner lumen connecting the handle and the delivery capsule; and
      an integrated introducer slidably disposed about the inner lumen, the integrated introducer comprising:
         a sheath comprising a proximal end, a distal end, an inner diameter, and an outer diameter; and
         a hub located at the proximal end of the sheath,
      wherein the inner diameter of the sheath is smaller than the outer diameter of the delivery capsule,
      wherein the distal end of the sheath is rigid and cannot slide over any portion of the delivery capsule, and
      wherein the proximal end of the delivery capsule contacts the distal end of the sheath in an insertion configuration;
   inserting the delivery system into a body lumen;
   advancing the delivery capsule distally such that it breaks contact with the sheath;
   maneuvering the delivery capsule to a deployment location; and
   deploying the medical device at the deployment location.

21. The method of claim 20, further comprising disconnecting the integrated introducer from the handle.

22. The method of claim 20, wherein the hub further comprises a locking element and the method further comprises sliding the integrated introducer along the inner lumen and locking the integrated introducer in place by activating the locking element.

* * * * *